(12) United States Patent
Brodnick (10) Patent No.: US 7,697,982 B2
(45) Date of Patent: Apr. 13, 2010

(54) SYNCHRONIZATION TO A HEARTBEAT

(75) Inventor: Donald E. Brodnick, Cedarburg, WI (US)

(73) Assignee: General Electric Company, Schenectady, NY (US)

( * ) Notice: Subject to any disclaimer, the term of this patent is extended or adjusted under 35 U.S.C. 154(b) by 1016 days.

(21) Appl. No.: 11/412,283

(22) Filed: Apr. 27, 2006

(65) Prior Publication Data

US 2007/0255150 A1    Nov. 1, 2007

(51) Int. Cl.
*A61N 1/39* (2006.01)
(52) U.S. Cl. .............................. 607/5; 600/518
(58) Field of Classification Search .............. None
See application file for complete search history.

(56) References Cited

U.S. PATENT DOCUMENTS

| | | | |
|---|---|---|---|
| 3,626,932 A | 12/1971 | Becker | |
| 3,821,948 A | 7/1974 | King | |
| 3,954,098 A | 5/1976 | Dick et al. | |
| 4,192,318 A | 3/1980 | Dam et al. | |
| 4,240,442 A | 12/1980 | Andresen et al. | |
| 4,616,659 A | 10/1986 | Prezas et al. | |
| 4,617,938 A | 10/1986 | Shimoni et al. | |
| 4,679,144 A | 7/1987 | Cox et al. | |
| 5,000,182 A | 3/1991 | Hinks | |
| 5,562,709 A | 10/1996 | White | |
| 5,999,850 A | 12/1999 | Dawson et al. | |
| 6,438,411 B1 | 8/2002 | Guttman et al. | |
| 6,871,094 B1 * | 3/2005 | Allen et al. | 607/5 |
| 2004/0220630 A1 | 11/2004 | Mongeon et al. | |

FOREIGN PATENT DOCUMENTS

WO    WO 0047279    *    8/2000

* cited by examiner

*Primary Examiner*—Carl H. Layno
*Assistant Examiner*—Jon-Eric C. Morales (57) ABSTRACT

An apparatus for producing a trigger signal, for use with a medical device, that is synchronized to a heartbeat in a subject of interest. The apparatus includes a sensor for obtaining ECG data from the subject of interest. The apparatus further includes a processor coupled to the sensor, with the processor configured to generate the trigger signal based on a real time analysis of the ECG data and to only synchronize and transmit the trigger signal to the medical device if a pre-selected characteristic of the heartbeat is identified. The apparatus further includes and a display device coupled to the processor and configured to display the ECG data and the trigger signal.

27 Claims, 8 Drawing Sheets

SYNCHRONIZATION TO A HEARTBEAT

FIELD OF THE INVENTION

The present invention relates generally to the field of synchronizing a process to a heartbeat and specifically to production of a trigger signal used with a medical device that is synchronized to a heartbeat.

BACKGROUND OF THE INVENTION

For numerous applications it is desirable to have an apparatus and method to synchronize a process to the heartbeat of a human or other animal. A patient monitor or other equipment may monitor an electrocardiogram (ECG) and by use of electronic circuitry and a software signal processing algorithm produce a synchronization pulse, also called an R-wave trigger or an R-wave gate, that can be used by integral circuitry or by additional externally attached equipment.

One application is cardiovascular where the heart has upper chambers, the atria, which are in a disorganized rhythm of contraction known as Atrial Fibrillation (AFIB). Lower chambers, the ventricles, do have an organized rhythm of contraction. In this case a shock delivered at the proper moment can reorganize the atria and terminate this dangerous heart rhythm. Because the lower chambers, the ventricles, are the major pumping muscles and in this AFIB rhythm the ventricles are in an organized pumping rhythm, AFIB is not immediately dangerous. For the cardioversion process, however, if the shock is delivered at an improper moment, the ventricles are vulnerable to converting to a disorganized contraction known as Ventricular Fibrillation (VFIB) which is immediately dangerous since all pumping action ceases. Permanent brain damage occurs within a few minutes. Therefore it is essential to deliver the cardioversion shock at the most proper and safe moment. Current device standards understand and guide the device manufacturer on this issue. Cardioversion shock should be synchronized to the period of the R wave of the ECG and not later than 30 milliseconds after the peak of the R wave.

Another application is image acquisition. Images acquired by machines like Computerized Tomography (CT) scanners or Fluoroscope scanners or ultrasound benefit from combining images collected from a consistent moment in the cycle of numerous heartbeats. An example is the moment in each heartbeat where the muscle is completely relaxed, diastole. If a trigger is available at the instant of each R-wave, the imaging equipment can take a series of images at a fixed delay. Combining multiple images can provide a much higher quality image where random noise has been significantly reduced.

Another application example is non-invasive blood pressure measurement. Here a device such as a cuff and microphone are components in a system that observes the acoustic response (Korotkoff sounds) of an artery in the arm as pressure in a cuff is reduced. At each heartbeat when the cuff pressure is in a certain range some blood can squirt through the artery and make the sound. A detector has a much better confidence of detecting these sounds if an independent trigger is available to indicate the moment of each heartbeat.

For many applications, but not all, a trigger is desired only for the normal heartbeats. The heart can generate spontaneously abnormal heartbeats, such as Premature Ventricular Contractions (PVC) or Premature Atrial Contractions (PAC) and several others. These abnormal heartbeats, also called ectopic heartbeats, are frequently ineffective or less effective at pumping blood. The path of cell to cell depolarization of the heart muscle is usually different for these beats and so the actual mechanical motion of the heart will be different. For most imaging techniques it is desirable that no image be added to the ensemble average for these abnormal beats. Also for the blood pressure application, R wave gates on abnormal beats are not helpful since blood pressure production from these beats is significantly different from normal beats.

An important clarification is that the component of the ECG waveform known to signify the electrical depolarization and the mechanical contraction of the main heart muscles is called the QRS component. The R-wave is generally understood to be the largest positive part of the QRS. For triggering systems, if the largest part of the QRS is a negative wave, technically a Q or an S wave, it is desirable to trigger on the negative wave. Such a system is still referred to as a R-wave trigger or gate. Frequently the terms R-wave or QRS are used interchangeably.

Conventional R-wave triggers suffer from a sensitivity to noise in the ECG, or lack of consistency in the time relationship of the trigger to the R-wave, and/or lack of specificity to normal heartbeats. More sophisticated arrhythmia analysis algorithms do reliably detect heartbeats and usefully classify beats as normal or abnormal, but these more sophisticated algorithms generally require substantially more computer power (more central processing unit (CPU) cycles per second and more memory usage for the program and data) and generally have a significant delay in determination; not less than 200 milliseconds and more typically one to two seconds delay before classification is known.

Therefore, there is a need to have a method and apparatus that can detect and classify an R-wave as normal or abnormal. There is also a need for this detection and classification to occur within about 30 milliseconds. There is also a need for this detection and classification to be as simple and efficient as possible for incorporation in small, low cost, and low power equipment in addition to applications in larger and more expensive equipment.

SUMMARY OF THE INVENTION

One embodiment of the invention relates to an apparatus for producing a trigger signal, for use with a medical device, that is synchronized to a heartbeat in a subject of interest. The apparatus includes a sensor for obtaining ECG data from the subject of interest. The apparatus further includes a processor coupled to the sensor, with the processor configured to generate the trigger signal based on a real time analysis of the ECG data and to only transmit the trigger signal to the medical device if a pre-selected characteristic of the heartbeat is identified. The apparatus may further include a display device coupled to the processor and configured to display the ECG data and the trigger signal.

Another embodiment of the invention relates to a method for producing a trigger signal, for use with a medical device, that is synchronized to a heartbeat in a subject of interest. The method includes the steps of sensing ECG data from the subject of interest; processing the ECG data in a computer and generating the trigger signal based on a real time analysis of the ECG data and to only transmit the trigger signal to the medical device if a pre-selected characteristic of the heartbeat is identified. Another embodiment includes the step of displaying the ECG data and the trigger signal.

Another embodiment of the invention relates to an apparatus for producing a trigger signal that is synchronized to a heart beat in a living organism, comprising a sensor for obtaining ECG data from the living organism. A processor coupled to the sensor, with the processor configured to generate the trigger signal based on a real time analysis of the ECG data and to only transmit the trigger signal to a medical device if a pre-selected characteristic of the heartbeat is identified. A display device coupled to the processor and configured to display the ECG data and the trigger signal. An input device coupled to the processor, including an user interface.

DETAILED DESCRIPTION OF THE EXAMPLE EMBODIMENTS

Figure 1:
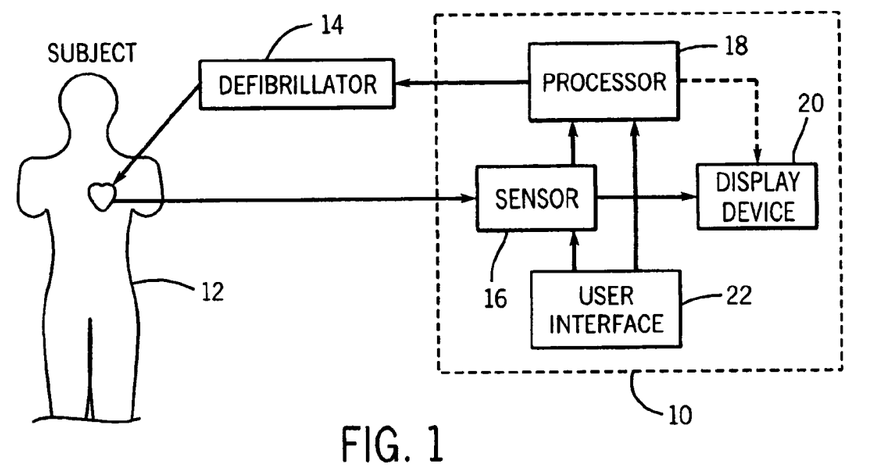
FIG. 1 is a block diagram of a defibrillator apparatus for producing a trigger signal that is synchronized to a heartbeat according to one example embodiment.
Figure 2:
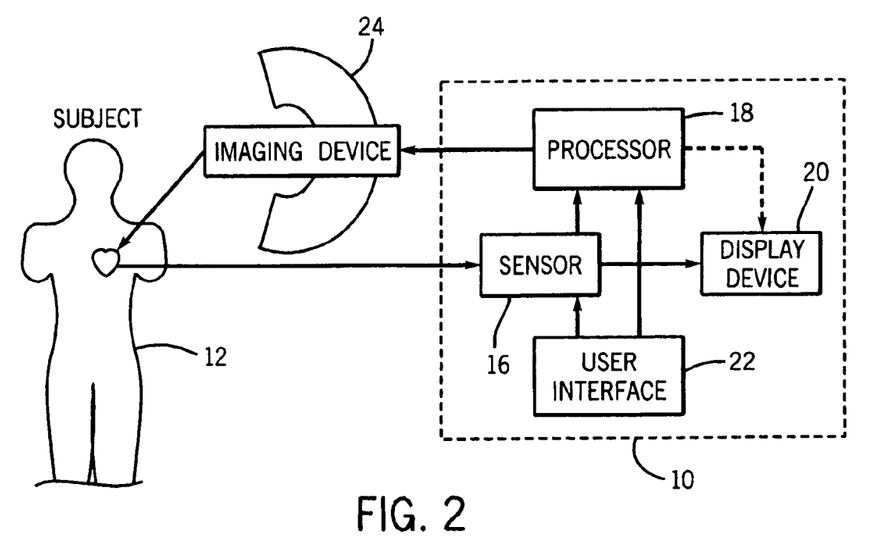
FIG. 2 is a block diagram of an image synchronization apparatus for producing a trigger signal that is synchronized to a heartbeat according to one example embodiment.

Referring to FIGS. 1 and 2, apparatus 10 is intended to provide a real-time trigger signal from a single channel of an ECG. Such a trigger may be useful in multiple applications where devices must be activated in synchronization with the subject's heart.

FIG. 1 illustrates an example embodiment for heartbeat signal synchronization where an energy pulse is delivered to the heart of subject of interest 12 by a defibrillator device 14 in order to stop an atrial arrhythmia. The pulse may be synchronized to the heartbeat signal to reduce the risk of stimulating the heart into a more dangerous ventricular arrhythmia. In the illustrated embodiment the synchronization pulse is intended to be minimally delayed from the heartbeat of subject 12. The jitter in timing of the synchronization pulse (variability in precise time relationship of each pulse to the start of the heartbeat) is unimportant since one or very few energy pulses from defibrillator 14 may be synchronized.

Subject of interest 12 is coupled via a connection for electrocardiographic (ECG) voltage signals, such as electrodes, to apparatus 10 containing a sensor 16, a processor 18, a display device 20, and a user interface 22. While the illustrated example embodiment shows subject of interest 12 to be a human, in other exemplary embodiments subject of interest 12 may be another living organism, such as a dog, cat, or horse. In still other exemplary embodiments the subject of interest may be non-animal subjects such as simulators used for testing purposes which generate a heartbeat ECG signal for analysis.

Sensor 16, for example an ECG acquisition system, may be composed of isolation circuits, amplifiers, filters, and digitizers of any past, present, or future form known in the art. A digital waveform data stream of ECG data may be passed to processor 18 where an R-wave synchronization algorithm may be performed.

Processor 18 is generally configured to generate a trigger signal based on a real-time analysis of ECG data and to synchronize and transmit the trigger signal to a medical device, in this case defibrillator 14, if the heartbeat is normal. Processor 18 may perform this function by generating pulses or other communication indicators which may be output from the monitoring instrument. In various exemplary embodiments, processor 18 may be any suitable processor capable of processing incoming data with an algorithm and optionally capable of outputting results in a visual or otherwise user-readable format.

Display 20 may receive indications from processor 18 that can be combined with the ECG waveform in a way that a human operator of the instrument can confirm that R wave triggers are associated to the appropriate heartbeats in the ECG. If the waveform and trigger display is unsatisfactory, the user may select other ECG leads or reset the algorithm run on processor 18 to relearn on subsequent heartbeats via user interface 22. In various exemplary embodiments, display device 20 may be any suitable display device that can be coupled to processor 18 and display an ECG waveform.

FIG. 2 illustrates an exemplary embodiment where an imaging device 24; such as a computerized tomography (CT) scanner, a magnetic resonance (MR) scanner, an X-ray or fluoroscope machine, an ultrasound machine, or any other suitable imaging device, for example; may need to be synchronized to the heartbeat of subject 12. Image quality may be improved by taking multiple images and averaging them together. By synchronizing all the images to the heart it may be in the same phase of contraction for each image. After an image for one phase of the heart, such as diastole (relaxed), has been assembled from many heartbeats, the process may be repeated at a different delay from the synchronization pulse in order to average many more heartbeats into an image of a different phase of heart contraction such as systole (squeezing). For good signal quality these synchronization pulse may have minimum jitter (precisely repeatable time relationship to every heartbeat) at the cost of additional delay.

An image sequence that appears to be many frames of a single heartbeat may be assembled from many heartbeats if imaging device 24 cannot obtain images fast enough to take all images in a single heartbeat. In this exemplary embodiment a precise low jitter trigger may be used for each heartbeat with imaging device 24 taking one image per heartbeat while delay increases in small steps. The exemplary embodiments of FIG. 1 and FIG. 2 illustrate why a fast R-wave trigger system may benefit from a configuration into more than one mode, one to minimize delay and another to minimize jitter.

Figure 3:
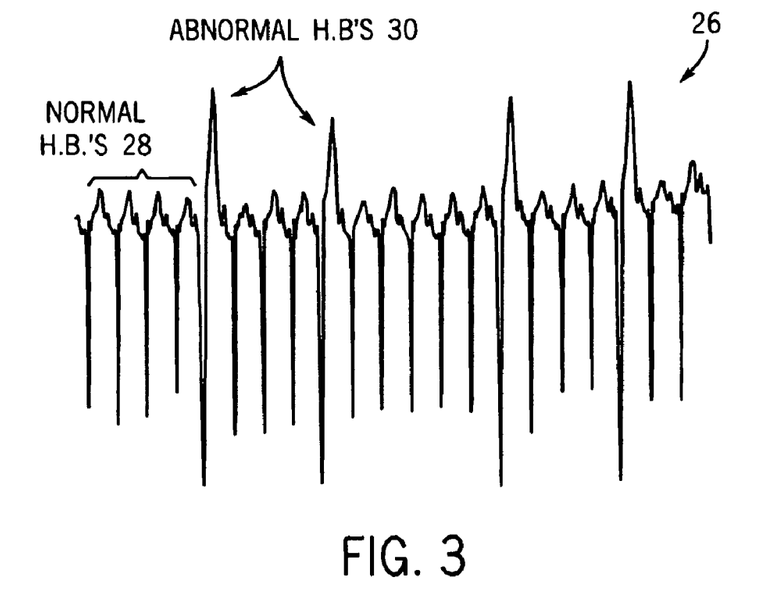
FIG. 3 is a waveform of an ECG signal that may be used for synchronization according to the example embodiments of FIG. 1 and FIG. 2.

Referring to FIG. 3, a ten second record 26 of a fast heart rate ECG with many normal heartbeats 28 and four abnormal heartbeats 30 are shown. For purposes of this application, a "normal" heartbeat is defined as a heartbeat with electrical and mechanical behavior which is typical and efficacious for a patient. In other words, a heartbeat where the heart contracts in a most healthy way to usefully pump blood. Preferably, the patient has many of these heartbeats and they are all very similar to each other. The patient can be a human or an animal, or a "normal" heartbeat ECG signal can be generated by a simulator for testing purposes. An "abnormal," "ectopic," or "irregular" heartbeat is defined as a heartbeat with electrical and mechanical behavior which is less efficacious for the patient. These heartbeats contract in an abnormal fashion which compromises the pumping of blood. Preferably the patient has fewer abnormal heartbeats than normal beats. Normal heartbeats generally have a contraction of the left and right ventricles of the heart simultaneously causing a shorter total duration of contraction. This is evidenced in the ECG signal as a narrow width QRS complex (60-120 milliseconds). Abnormal heartbeats generally may have a contraction of one ventricle following the contraction of the other ventricle causing the extended total duration of contract. This is evidenced in the ECG signal as a wide QRS complex (120-200 milliseconds). Such characteristics of a heartbeat can be identified during the analysis of the ECG heartbeat signal. Such characteristics can be pre-selected for analysis and when identified during the analysis of the ECG signal data, the trigger signal can be generated as more fully described below.

Figure 4:
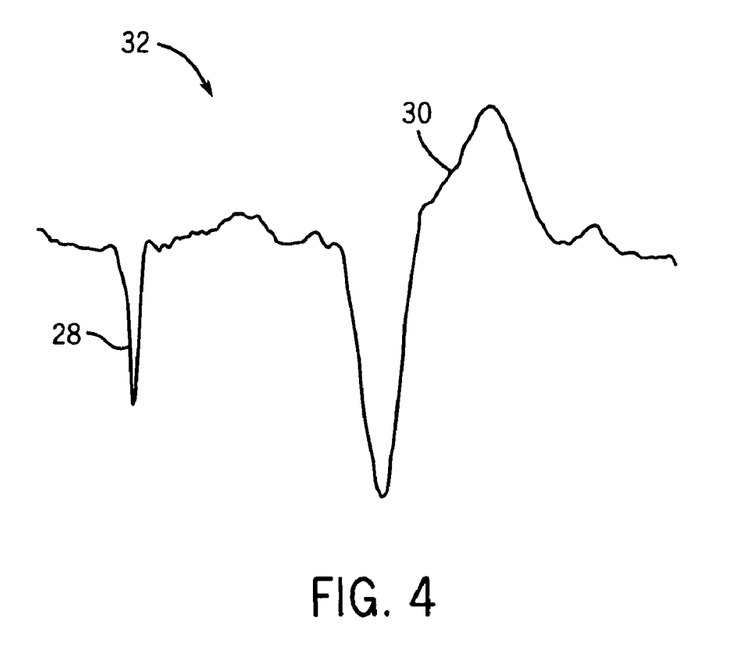
FIG. 4 is a waveform showing a close up view of an abnormal heartbeat with a preceding normal heartbeat according to the example embodiment of FIG. 3.

Referring to FIG. 4, an expanded time view 32 of just two of the heartbeats from FIG. 3, an abnormal and a normal heartbeat, is shown. It is noted that FIG. 5 and FIG. 6 are generally at the same scale and of the same two heartbeats as FIG. 4.

Figure 5:
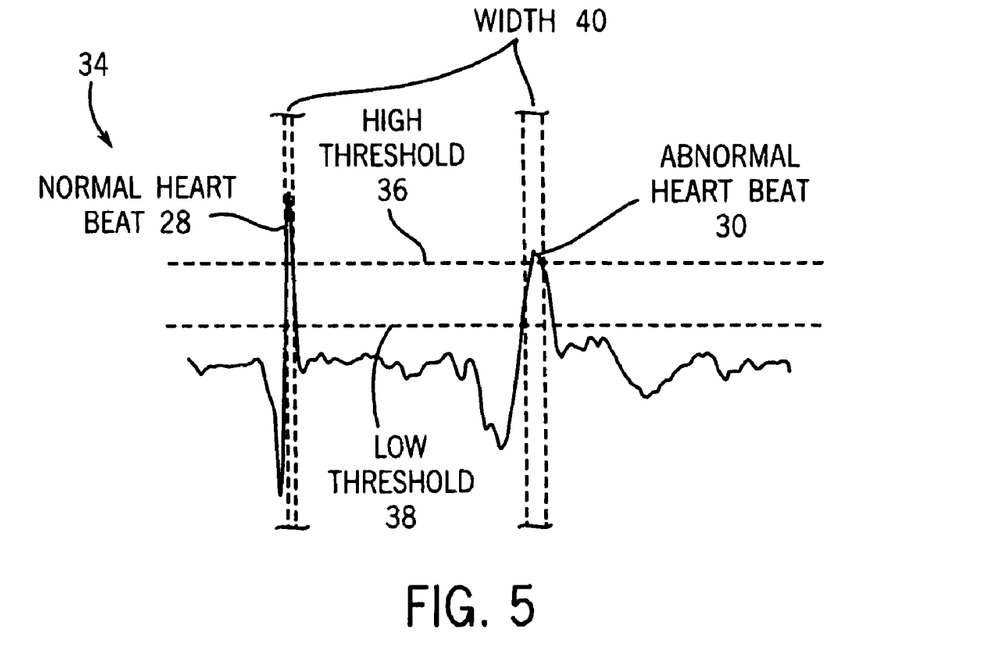
FIG. 5 is a waveform showing the first derivative (slope) of an ECG signal and threshold crossings according to the example embodiments of FIG. 1 and FIG. 2.

Referring to FIG. 5, a waveform 34 of the first derivative, or slope, of the waveform in FIG. 4 is shown in a minimize jitter mode. As shown in FIG. 4, normal heartbeat 28 is basically a negative triangle. The triangle has an initial negative slope (going down to the lowest point) followed by a positive slope (going back up to the baseline). These negative and positive slopes or derivatives are illustrated in waveform 34. When the minimize jitter mode is active, positive slope thresholds may be selected. In the illustrated exemplary embodiment, a high magnitude threshold 36 is about 62% of the peak level and a low magnitude threshold 38 is about 25% of the peak level, marked as horizontal dotted lines. Even though abnormal beat 30 has lower peak slopes it may still just cross high threshold 36. In other exemplary embodiments, high threshold 36 may be higher or lower than about 62% of the peak level and low threshold 38 may be higher or lower than about 25% of the peak level as long as jitter is reduced.

A width 40, for example a QRS width, may be computed when the slope signal exceeds high threshold 36. Width 40 may be measured from the moment the slope crosses low threshold 38 to the moment the slope falls below high threshold 36 (shown by vertical dotted lines). Width 40 of abnormal beat 30 is generally wider than that of normal beat 28; in the illustrated example embodiment, 72 milliseconds versus 28 milliseconds. This difference in width makes it possible for the algorithm run by processor 18 to segregate the two beat detections and produce relatively high confidence trigger indications only for the beats that have widths 40 close to the median widths of all beats, which may be the width of the most frequent type of beats, or normal heartbeats.

Figure 6:
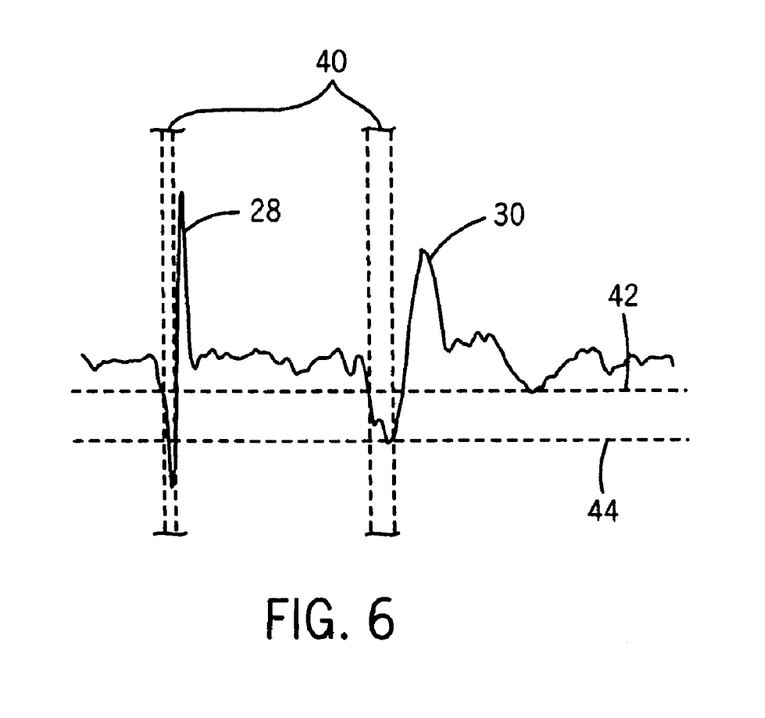
FIG. 6 is a waveform showing the slope signal of FIG. 5 that is processed using the negative thresholds according to the example embodiments of FIG. 1 and FIG. 2.

In FIG. 6 the same segment of ECG as in FIG. 5 is shown, but this time with a high and low threshold 42 and 44, respectively, selected by the minimize delay mode. This mode has selected negative thresholds because these will generate triggers earlier in each heartbeat cycle despite the risk of increased jitter. For each heartbeat 28 and 30, the second vertical dotted line may be a relatively high confidence trigger if width 40 is correct; this may happen even before the heartbeat complex is half over.

Thresholds 42 and 44 may cause increased jitter in the triggers. For negative thresholds, low threshold 42 is closer to the zero level of the signal and may actually graph above high threshold 44. After abnormal beat 30, a component of the signal may come close to and skims along low threshold 42, as illustrated in FIG. 6, and abnormal heartbeat 30 may just come up to and skim along high threshold 44. The bins of the histogram near these threshold levels may have high counts of samples and indicate increased ambiguity. A very little amount of noise added to the signal may cause abnormal heartbeat 30 to cross or not cross high threshold 44 when it otherwise would not. When high threshold 44 is crossed, a small amount of noise may cause the time of the crossing to shift earlier or later making the width measurement unreliable. For these reasons, when the minimize jitter learning mode was used in FIG. 5, negative thresholds were rejected as being more ambiguous than positive thresholds.

Figure 7:
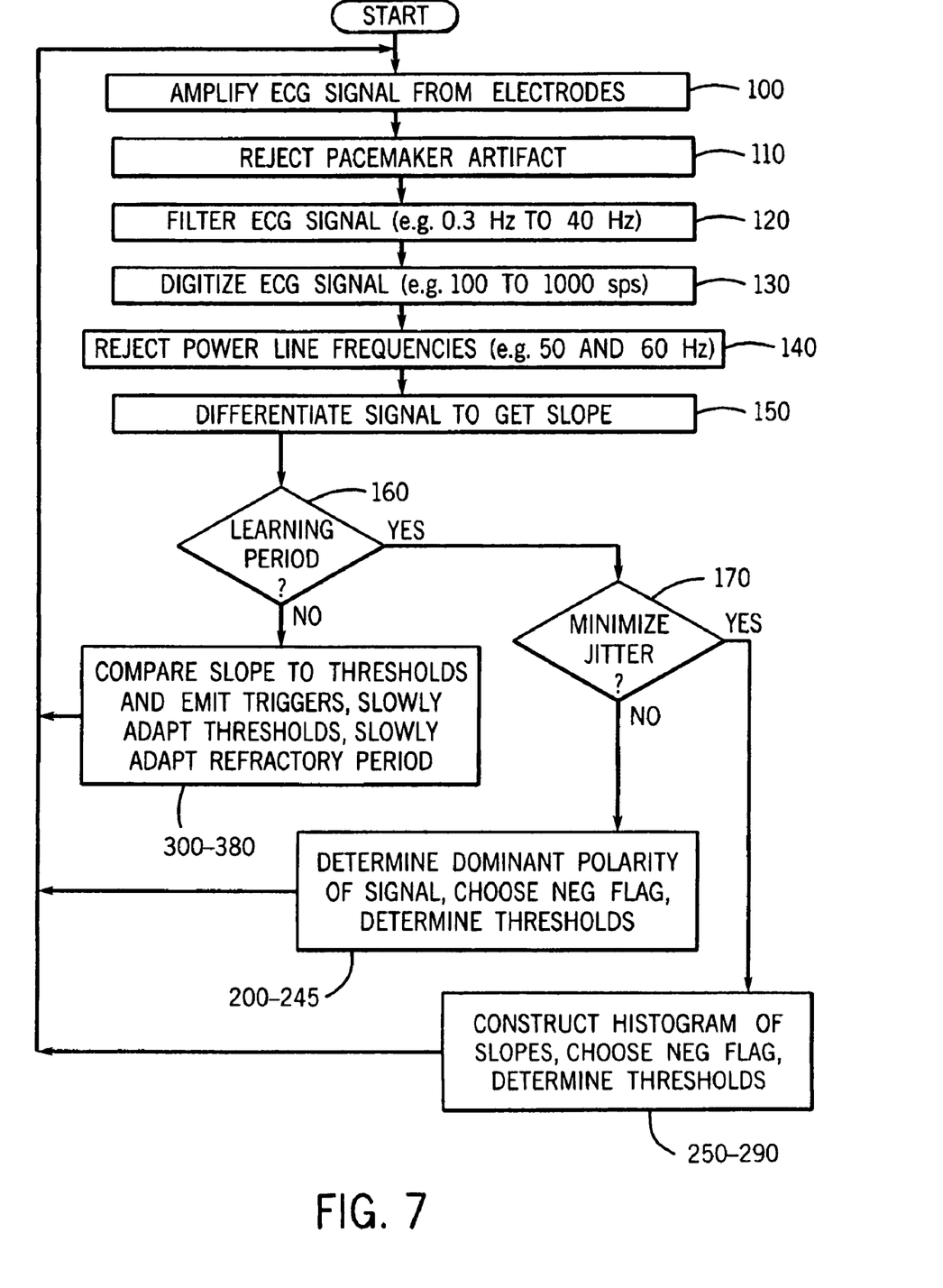
FIG. 7 is a flowchart showing the high-level operation of the example embodiments of FIG. 1 and FIG. 2.

Referring to FIG. 7, a high-level flowchart representing circuitry performing the synchronization method is shown. At block 100, the ECG signal from the electrodes on subject 12 may be amplified. In one exemplary embodiment, the amplification may be achieved by any past, present or future ECG amplifier with a gain of between about 100 to 1000. In other exemplary embodiments, the amplifier may be isolated from subject 12 for safety or include typical circuits to block or shunt electrostatic shock. Block 100 may also represent lead selection circuitry and/or lead fail detection circuitry.

At block 110, the passage of electronic implanted pacemaker artifacts may be blocked. Unblocked, these artifacts may confound heartbeat detectors since the amplitude can be larger than the ECG heartbeat.

At block 120 the ECG signal may be filtered by any past, present or future filter. In one exemplary embodiment, the filter may be not be more than one or two poles for each edge. In another exemplary embodiment a two pole 40 Hz low pass combined with a one pole 0.3 Hz high pass may be used. The filter may be used to center the signal in a digital converter range and limit the frequency content to the speed of the converter (anti-alias).

At block 130, the ECG signal may be digitized so that samples of the signal may be processed by processor 18. In one exemplary embodiment, rates of 100 samples per second (sps) may be used. In other example embodiments, faster rates may be beneficial, but sample rates exceeding 1000 sps are unlikely to add benefit while adding burden to processor 18.

At block 140, power line frequencies may be rejected by an optional power line filter. In one exemplary embodiment the filter may be a notch filter at 50 Hz and/or 60 Hz. In other exemplary embodiments, the filter may be higher harmonics of both frequencies if these frequencies would be in the pass band of the signal, that is if block 120 was passing more than 40 Hz bandwidth. Even with block 120 performing a 40 Hz low pass filter, the power line filters may be desirable since a one or two pole 40 Hz low pass filter may attenuate higher frequencies but may not eliminate them completely.

At block 150, a calculation of a first difference of the ECG voltage is performed to produce a slope signal. Such a slope signal may diminish the interference from breathing artifacts and motion artifacts. The slope signal may also diminish the interference of the T wave component of the ECG.

It is noted that in various exemplary embodiments, the sequence of blocks 100 to 150 may be reordered so that filters are performed earlier with hardware circuits or optionally later as software routines.

Block 160 is a decision point to route execution into a learning process. In one exemplary embodiment, such a process may utilize ten seconds of ECG data, while in other exemplary embodiments greater than ten seconds or less than ten seconds may be used. In various exemplary embodiments, a system utilizing the synchronization method may restart the algorithm, either at the manual request of a human, or automatically when there has been a change in ECG leads or an interruption of ECG lead connection. When such a reset is called for this decision point may again route execution into a learning mode. Because there are two learning modes, the algorithm may be restarted to activate the alternative learning mode. In each case, during the learning period the algorithm may not emit trigger indications (pulses) until the period has expired.

Block 170 is a decision point to route execution into the desired learning mode. One mode (blocks 200-245) is to configure the algorithm to provide triggers of minimum delay after the start of the R wave. This mode may contain more jitter in the trigger times and thus may be desirable for synchronizing a defibrillator. The other mode (blocks 250 285) is to minimize jitter and may accept more delay. This mode may be desirable for image synchronization. In other exemplary embodiments, more than the two modes given here may be included, such as a hybrid mode to combine some aspects of each of the minimize jitter and minimize delay modes.

If learning has been completed, block 160 routes execution into the triggering logic (blocks 300 380). Here each digitized sample may be considered with stored data to decide whether any of three different triggers should be indicated at that instant. For real-time operation, as soon as the triggering logic is complete, the algorithm may wait until the next signal sample is available from the converter and filters and repeat the process. Although a strength of this algorithm is its utility in real-time applications, in other exemplary embodiments the signal processing and good performance level may be useful in non real-time applications where minimum processing burden (speed and memory) is desirable.

Figure 8:
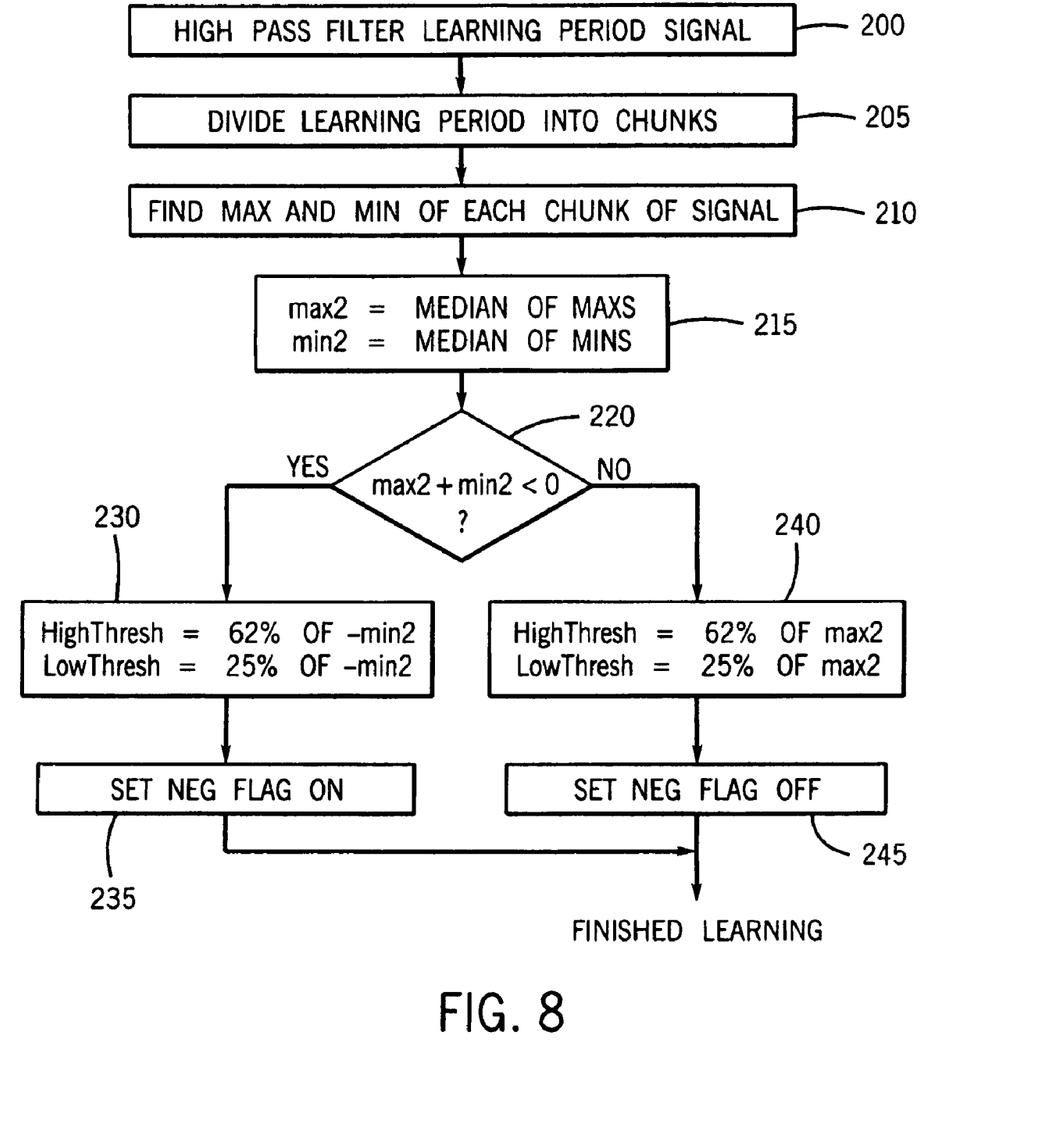
FIG. 8 is a flowchart illustrating a minimize delay learning mode according to the example embodiment of FIG. 7.

Referring to FIG. 8, the logic used for a minimize delay mode is illustrated. Block 200 may collect a high pass filtered signal according to the designated learning period. In one exemplary embodiment, the signal may be filtered by a one pole filter with a time constant of about 250 ms and a 3 dB corner frequency of about 0.64 Hz. This filtering may be useful to reduce baseline drift and respiratory baseline artifacts while preserving the polarity and configuration of normal heartbeats 28.

Block 205 divides the filtered signal of the learning period into separate chunks of a smaller period. In an exemplary embodiment where the learning period is ten seconds, each chunk may be two seconds, for example. This division may be regardless of heartbeats, but rarely will the heart rate be so low that in embodiments with a two second or greater chunk less than one heartbeat occurs. In an embodiment with five two second chunks, any two of the chucks may have some artifact or abnormal heartbeats 30, but when the median of measurements across the five chunks is taken, the abnormalities may be discounted.

Block 210 may record a maximum and minimum signal level for each signal chunk. Because of the earlier high pass filter, the minimum signal level peaks may all be negative numbers.

Block 215 selects the median of the five maximum levels and the median of the five minimum levels. This may well characterize the dominant polarity and size of normal heartbeats. The effects of noise and abnormal beats may detrimentally affect these levels if more than about 40% of the signal is contaminated. In such a case the trigger performance may be poor and an operator of this equipment may choose to restart the algorithm so that learning occurs again on cleaner signal or the operator may choose to select a different ECG lead and restart the algorithm. It is noted that in other exemplary embodiments, more or fewer than five maximum or minimum levels may be selected when calculating the medians of the maximum and minimum values.

Block 220 may decide whether normal heartbeat 28 is predominantly a positive wave or a negative wave. Because the median of the minimum values is a negative number the sum of the medians of the maximum values and minimum values will be less than zero if the normal heartbeat is predominantly a negative wave.

Block 230 may be executed if normal heartbeat 30 is predominantly a negative wave. If so, the leading edge of the heartbeat will tend to be a negative slope and for minimum triggering delay the triggering logic may look for the large negative slope. In one exemplary embodiment, thresholds may be set at the low and high levels of 25% and 62% of the peak amplitude, while in other embodiments, higher or lower thresholds may be set.

Block 235 sets a NEG flag so that the triggering logic will know to look only at the negative slopes.

Block 240 is similar to block 230 except it may have been determined that normal heartbeats 28 are predominantly positive waves. As such, the leading edge slope is a positive value and thresholds are set from the peak positive (max) amplitude.

Block 245 clears the NEG flag so that the triggering logic will know to look only at the positive slopes.

Figure 9:
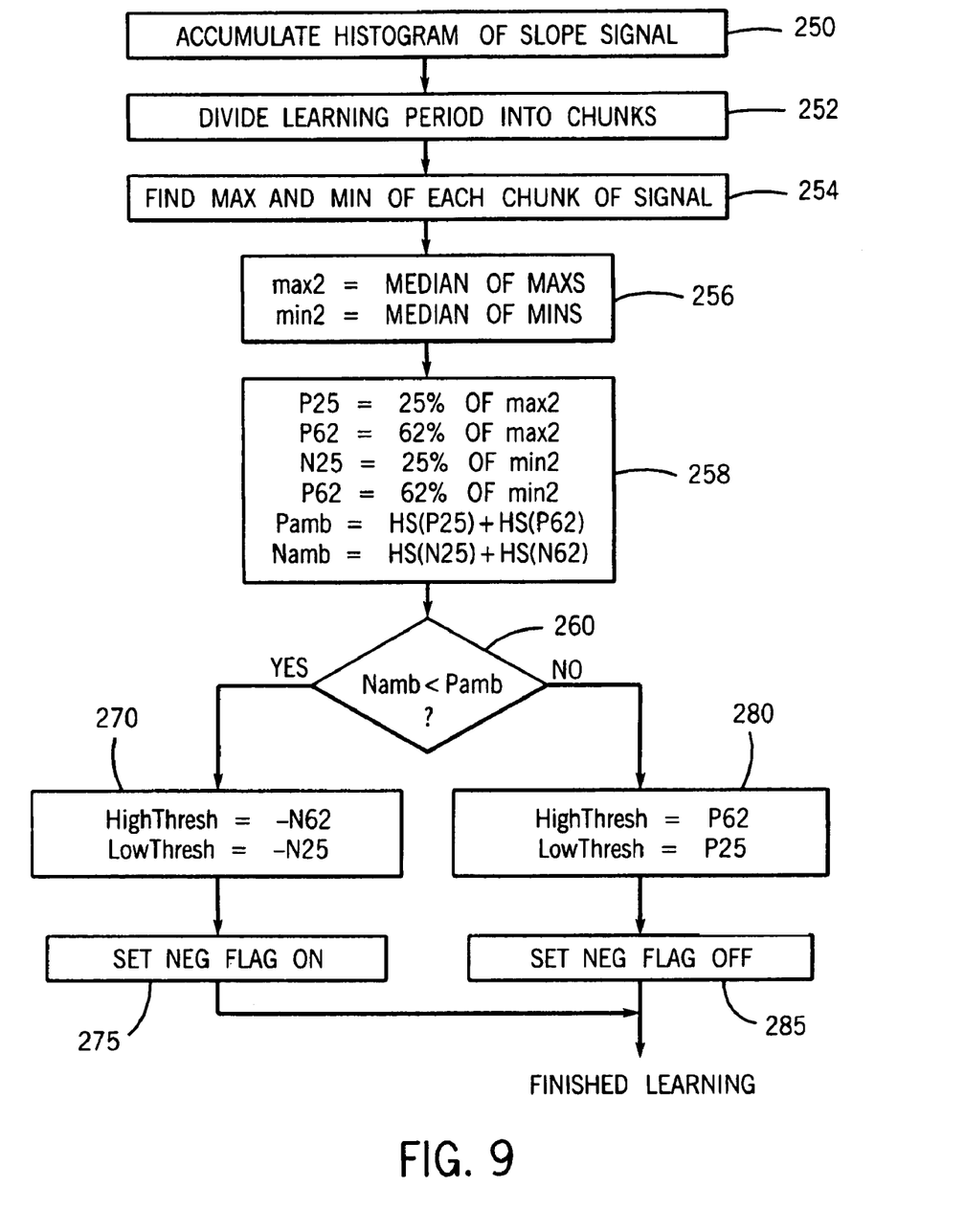
FIG. 9 is a flowchart illustrating a minimize jitter learning mode according to the example embodiment of FIG. 7.
Figure 10:
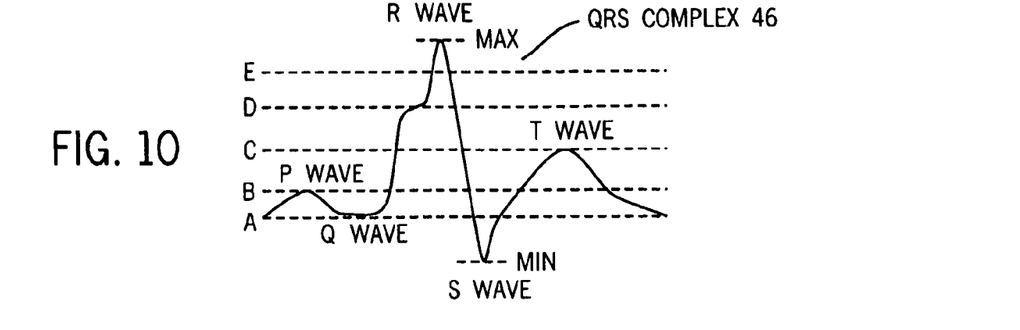
FIG. 10 is a QRS complex used by the minimize jitter learning mode of FIG. 9 according to one example embodiment.
Figure 11:
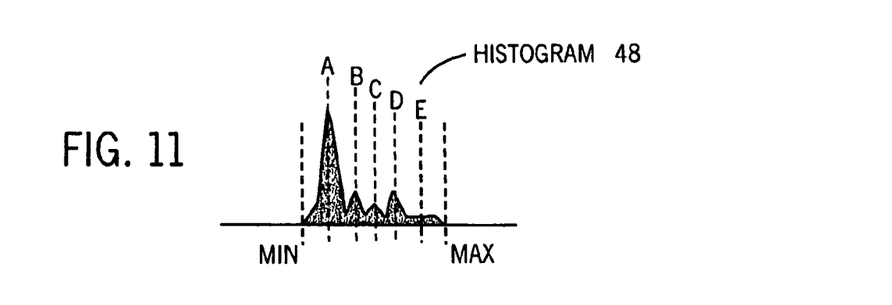
FIG. 11 is a histogram of ECG values created by the learning mode of FIG. 9 according to one example embodiment.

Referring to FIG. 9-11, the logic behind a minimize jitter mode is illustrated along with an example QRS complex 46 of an ECG and a histogram 48 identifying the least ambiguous trigger thresholds or optimal threshold values.

Block 250 creates a histogram of the slope signal level. This may be accomplished by counting how many signal samples of the learning period are in each of a number of voltage ranges. In one exemplary embodiment, at 100 sps, there may be 1000 voltage samples in a ten second signal. In another exemplary embodiment, one of the bins of the histogram may be for all voltages in the 0 to 20 microvolt range. Several hundred samples may be counted in that bin because it is so close to the baseline of the signal. In this embodiment, another bin may contain the voltage range of 0 to −20 microvolts. This bin may also have a high count of samples, whereas some other bin of the histogram may count samples at voltages between 600 and 620 microvolts and have fewer samples, perhaps only one or two samples per heartbeat. In this example embodiment the sum of the counts in all the bins of the histogram may be 1000.

Blocks 252, 254, and 256 are functionally the same as blocks 205, 210, and 215 in the other learning mode. The learning period is divided into multiple chunks, the maximum peak level (max) and minimum negative peak level (min) is recorded for each chunk, and the median max and median min are selected.

Block 258 computes two candidate sets of thresholds. In the illustrated example embodiment where the threshold levels are 25% and 62% of a peak or median peak value, a set of positive thresholds P25 and P62 and a set of negative thresholds N25 and N62 are used. An ambiguity measure (Pamb or Namb) may also be computed for the positive set and the negative set. The ambiguity measure is a count of the samples in the signal that are near to the threshold level. If only a few samples are near a threshold then it is unambiguous whether a section of signal is above or below the threshold. Conversely, if many samples exist at voltage levels similar to the threshold then the signal may have many more sections that are crossing through the threshold or that linger near the threshold changing slowly. The representation HS(P25) indicates a histogram summation of a few bins above and below the bin containing the threshold level P25.

Block 260 may select, for the candidate threshold set, a positive or negative threshold that has the least ambiguity.

Block 270 continues execution if the negative threshold set is less ambiguous. In this case the negative threshold set may be retained for use by the triggering logic later.

Block 275 sets the NEG flag so that the triggering logic knows to look only at the negative slopes.

Block 280 continues execution if the positive threshold set is less ambiguous. In this case the positive threshold set is retained for use by the triggering logic later.

Block 285 clears the NEG flag so that the triggering logic knows to look only at the positive slopes.

The least ambiguous thresholds may be useful for minimizing jitter because if the threshold is set to a level that the signal passes through very quickly and infrequently, then a larger amount of noise can be added to the signal without causing the trigger time to shift earlier or later in the waveform. The least ambiguous threshold may be a trailing edge of the heartbeat complex, however, meaning that the trigger may be more delayed.

QRS complex 46 has a plateau near the level marked by D. If this level was used as a trigger threshold a small amount of noise added to the signal may cause the triggering time to shift forwards and backwards during the plateau interval. Histogram 48 indicates a peak in the distribution of samples at the level of D. Similarly other components of the ECG such as the P wave and the T wave may cause other peaks in the histogram (B and C) because of the number of samples at a similar level near the tops of these waves. The highest density of samples is usually near the baseline, level A and peak A in this example.

By inspecting histogram 48 of the distribution of slope levels and choosing a level where there is a low density of samples, such as E in this example, a threshold level can be chosen with a small likelihood of occurring in multiple different wave components of the ECG or occurring near a wave peak or plateau where a small amount of noise or variation in QRS axis or amplitude may shift the time relationship of the trigger. The low density position of histogram 48 may select the level where the ECG signal passes through the quickest and least often per heart beat. Although for simplification, FIG. 10 shows only one heart beat and is in terms of the ECG voltage, in another exemplary embodiment the slope signal ($1^{st}$ derivative of the voltage) may be processed, the threshold may be set at the lowest density level occurring in histogram 48, and histogram 48 may be formed from a learning period of data, such as ten seconds for example.

Two thresholds may be determined by this process provided that they are within about 20% of target levels at ⅝ths and ¼ of the peak amplitude. This process may be repeated for positive thresholds and negative thresholds. The threshold pair with the combined lowest density may be considered to have the lowest ambiguity and the commitment may then made to process only the polarity with least ambiguity.

Figure 12:
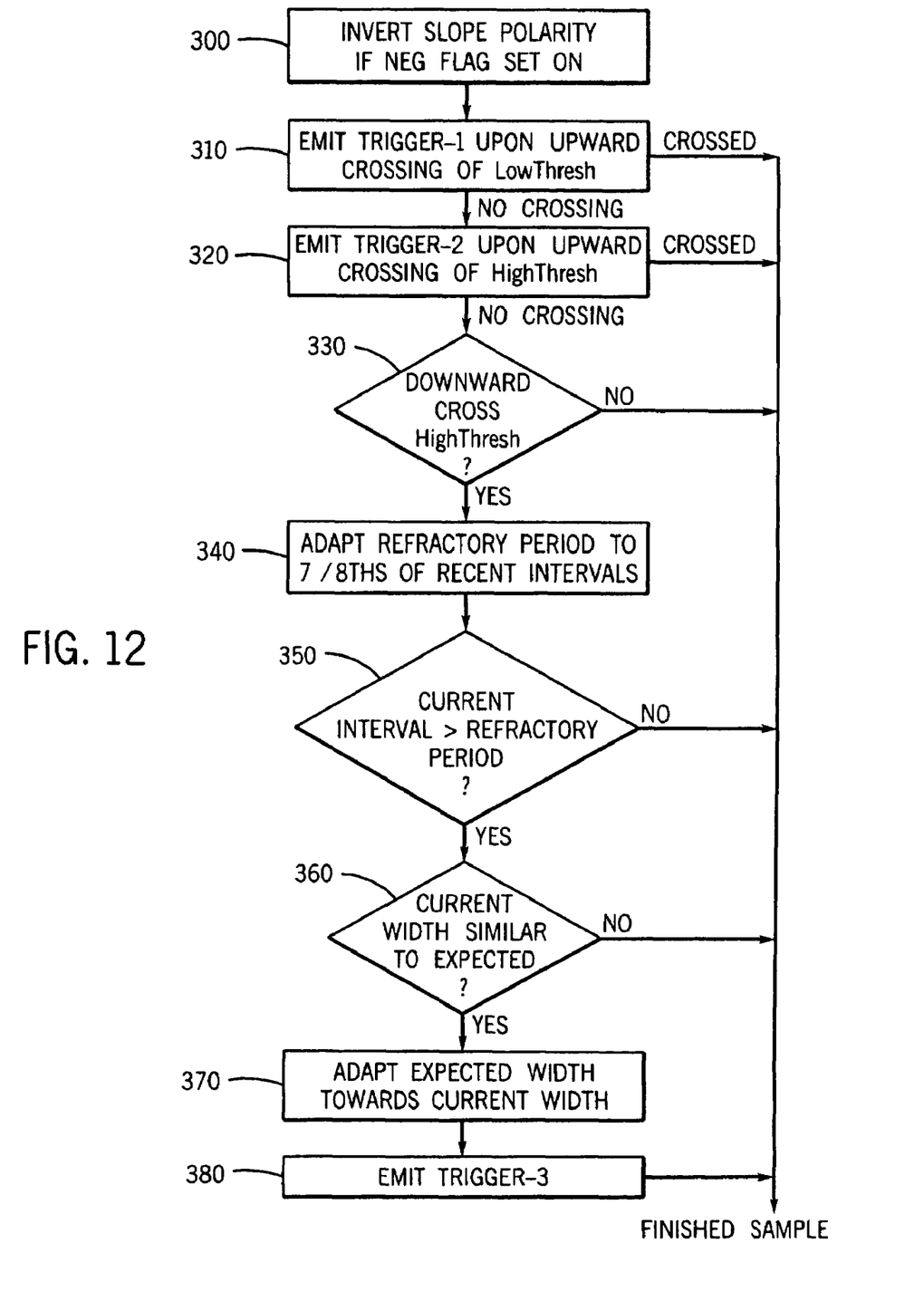
FIG. 12 is a flowchart illustrating triggering logic according to the example embodiment of FIG. 7.
Figure 13:
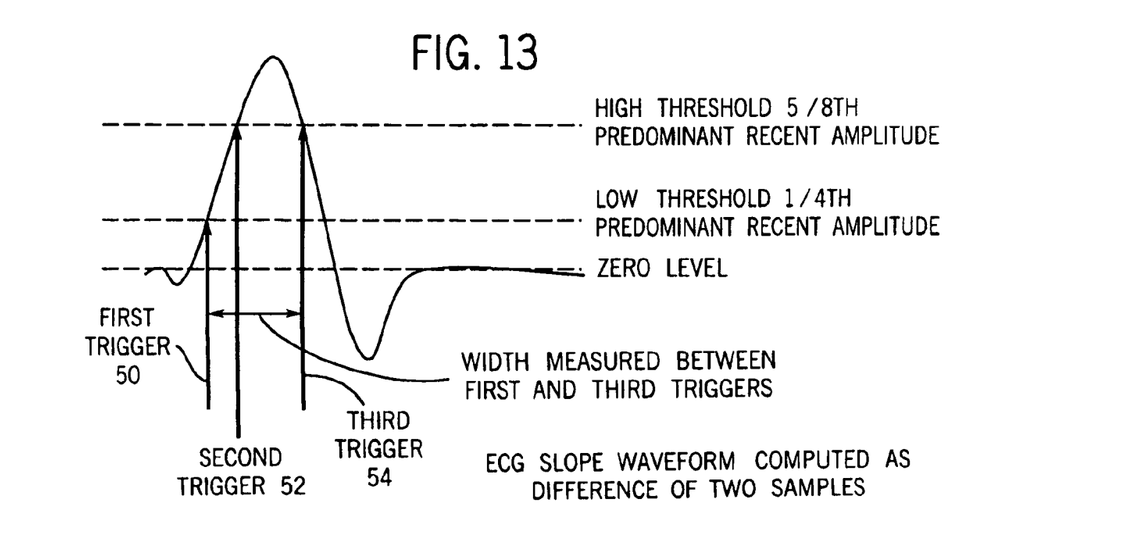
FIG. 13 is a waveform illustrating various thresholds and triggers for a slope signal used by the triggering logic in FIG. 10 according to one example embodiment.

Referring to FIGS. 12 and 13, a flowchart illustrating the triggering logic is given with a diagram showing thresholds and triggers for a QRS slope signal. Block 300 inverts the slope polarity signal if the NEG flag is set. This may be convenient and greatly simplify execution in processor 18 because all of the following logic can perform with only positive signals and thresholds.

Block 310 examines the slope signal and upon a crossing from below to above low threshold 38 or 42 the algorithm may return a first trigger 50 indicating a possible heartbeat. The equipment may use first trigger 50, if desired, to produce a hardware signal or a software signal sent to another piece of equipment. First trigger 50 has a low amount of qualification and may be generated often per heartbeat and at times unassociated with a heartbeat. In general, it may be present early in a heartbeat cycle and in some exemplary embodiments may be useful as a kind of set up or anticipation signal. In other exemplary embodiments, first trigger 50 may be ignored. This sample may also be counted as the first sample in QRS width 40.

Block 320 examines the slope signal and upon a crossing from below to above high threshold 36 or 44 the algorithm may return a second trigger 52 with a higher confidence level than that in block 310. Because this level is higher than low threshold 38 or 42, trigger 52 may occur less often and generally be expected only once per heartbeat. However, the only qualification is voltage level and trigger 52 may be emitted for normal heartbeats as well as abnormal heartbeats and artifacts.

Block 330 determines if this sample is the first sample to cross from above to below high threshold 36 or 44. If so, this marks the end of the samples in QRS width 40.

Block 340 determines the interval of time from this threshold crossing to the previous similar crossing. This current interval may be used to slowly adjust a saved value representing the median of recent intervals. A refractory period may be computed as ⅞ths of the recent intervals.

Block 350 determines if the current interval is longer than the refractory period. Intervals shorter than the refractory period may indicate abnormal heartbeats or artifacts.

Block 360 compares a currently measured QRS width to a saved value representing the median of recent QRS widths. If the current value is within a certain tolerance, in one exemplary embodiment about 20 milliseconds, then the current signal may be considered fully qualified as a normal heartbeat.

Block 370 may make a small adjustment to the saved value representing the median of recent QRS width features.

Block 380 returns a third trigger 54 signal. This is the fully qualified trigger that may be used by the system to identify normal heartbeats.

Although specific shapes of each element have been set forth in the drawings, each element may be of any other shape that facilitates the function to be performed by that element. For example, each ECG heartbeat may be of a different shape than any illustrated depending on the subject or equipment being used.

For purposes of this disclosure, the term "coupled" means the joining of two components (electrical or mechanical) directly or indirectly to one another. Such joining may be stationary in nature or movable in nature. Such joining may be achieved with the two components (electrical or mechanical) and any additional intermediate members being integrally defined as a single unitary body with one another or with the two components or the two components and any additional member being attached to one another. Such joining may be permanent in nature or alternatively may be removable or releasable in nature The present disclosure has been described with reference to example embodiments, however workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. An apparatus for producing a trigger signal that is synchronized to a heart beat in a subject of interest, the apparatus comprising:
   a sensor for obtaining ECG data from the subject of interest; and
   a processor coupled to the sensor, with the processor configured to generate the trigger signal based on an analysis of the ECG data and to only transmit the trigger signal to a medical device if a pre-selected characteristic of the heartbeat is identified,
   wherein the processor is further configured to learn to establish a trigger threshold and to select an ECG polarity signal, wherein the processor is further configured to determine one of a minimize delay mode to generate the trigger signal at a predetermined time point of the heart beat and a minimize jitter mode to generate the trigger signal at a time corresponding to a time point relating to the leading edge of the heart beat R-wave, and wherein the processor is further configured to generate a histogram of slope values of the ECG data to identify a threshold value for least jitter.

2. The apparatus of claim 1, including a display device coupled to the processor and configured to display the ECG data and the trigger signal.

3. The apparatus of claim 1, wherein the histogram is presented on the display device.

4. The apparatus of claim 1, wherein the processor is further configured to compute an ambiguity measure of threshold values to identify the threshold value for least jitter.

5. The apparatus of claim 1, wherein processor utilizes at least ten seconds of ECG data.

6. The apparatus of claim 5, wherein the trigger signal is not generated while the processor is using the ten seconds of ECG data.

7. The apparatus of claim 1, further comprising an input device coupled to the processor, including an user interface.

8. The apparatus of claim 7, wherein the trigger signal is initiated by the input device.

9. The apparatus of claim 1, wherein the subject of interest is a living organism.

10. A method for producing a trigger signal that is synchronized to a heart beat in a subject of interest, the method comprising the steps of:
    sensing ECG data from the subject of interest;
    processing the ECG data in a computer and generating the trigger signal based on an analysis of the ECG data and to only transmit the trigger signal to a medical device if a pre-selected characteristic of the heartbeat is identified;
    processing the ECG data to establish a trigger threshold and to select an ECG polarity signal;
    selecting one of a minimize delay mode to generate the trigger signal at a predetermined time point of the heart beat and a minimize jitter mode to generate the trigger signal at a time corresponding to a time point relating to the leading edge of the heart beat R-wave; and
    generating a histogram of slope values of the ECG data, and identifying threshold values for least jitter.

11. The method of claim 10, including the step of displaying the ECG data and the trigger signal.

12. The method of claim 10, displaying the histogram on a display device.

13. The method of claim 10, including the step of computing an ambiguity measure of the threshold values for least jitter to identify the threshold value for least jitter.

14. The method of claim 10, wherein the step of processing the ECG data utilizes at least ten seconds of ECG data.

15. The method of claim 14, wherein the trigger signal is not generated while the step of processing ECG data is taking place.

16. The method of claim 10, including the steps of providing an input device including an user interface and coupling the input device to the computer.

17. The method of claim 16, including the step of initiating the trigger signal with the input device.

18. The method of claim 10, wherein the subject of interest is a living organism.

19. An apparatus for producing a trigger signal that is synchronized to a heart beat in a living organism, the apparatus comprising:
    a sensor for obtaining ECG data from the living organism; and
    a processor coupled to the sensor, with the processor configured to generate the trigger signal based on an analysis of the ECG data and to only transmit the trigger signal to a medical device if a pre-selected characteristic of the heartbeat is identified;
    a display device coupled to the processor and configured to display the ECG data and the trigger signal; and
    an input device coupled to the processor, including an user interface,
    wherein the processor is further configured to learn to establish a trigger threshold and to select an ECG polarity signal, wherein the processor is further configured to determine one of a minimize delay mode to generate the trigger signal at a predetermined time point of the heart beat and a minimize jitter mode to generate the trigger signal at a time corresponding to a time point relating to the leading edge of the heart heat R-wave, wherein the processor is further configured to generate a histogram of slope values of the ECG data to identify a threshold value for least jitter.

20. The apparatus of claim 19, wherein the histogram is presented on the display device.

21. The apparatus of claim 19, wherein the processor is further configured to compute an ambiguity measure of threshold values to identify the threshold value for least jitter.

22. The apparatus of claim 19, wherein processor utilizes at least ten seconds of ECG data.

23. The apparatus of claim 22, wherein the trigger signal is not generated while the processor is using the ten seconds of ECG data.

24. An apparatus for producing a trigger signal that is synchronized to a heart beat in a subject of interest, the trigger signal for communication to a medical device, the apparatus comprising:

a sensor for obtaining ECG data from the subject of interest; and a processor coupled to the sensor, the processor operable to generate the trigger signal based on a trigger threshold and to transmit the trigger signal to the medical device, where the processor generates a histogram of slope values of the QRS complex as defined by the ECG data to identify the trigger threshold that minimizes jitter.

25. The apparatus of claim 24, wherein the histogram is illustrated on a display device.

26. The apparatus of claim 24, wherein processor computes an ambiguity measure of threshold values to identify the trigger threshold to minimize jitter.

27. The apparatus of claim 24, wherein the processor in a minimize delay mode generates the trigger signal at a predetermined time point of the heart beat, and wherein the processor in a minimize jitter mode generates the trigger signal at a time corresponding to a time point relating to a leading edge of an R-wave of the QRS complex.

* * * * *